United States Patent [19]
Knöfel et al.

[11] Patent Number: 5,196,591
[45] Date of Patent: Mar. 23, 1993

[54] PROCESS FOR THE PRODUCTION OF POLYNUCLEAR AROMATIC POLYAMINES

[75] Inventors: Hartmut Knöfel, Odenthal; Michael Brockelt, Leverkusen, both of Fed. Rep. of Germany; Marcel Petinaux, Pittsburgh, Pa.; Rudolf Uchdorf, Krefeld; Hans-Peter Schal, Dormagen, both of Fed. Rep. of Germany

[73] Assignee: Bayer Aktiengesellschaft, Leverkusen, Fed. Rep. of Germany

[21] Appl. No.: 863,613

[22] Filed: Apr. 6, 1992

[30] Foreign Application Priority Data

Apr. 13, 1991 [DE] Fed. Rep. of Germany ....... 4112131

[51] Int. Cl.$^5$ .................. C07C 209/78; C07C 209/84
[52] U.S. Cl. .................................... 564/331; 564/333; 564/334
[58] Field of Search .................. 564/331, 333, 334

[56] References Cited

U.S. PATENT DOCUMENTS

| | | | |
|---|---|---|---|
| 3,952,042 | 4/1976 | Knöfel | 260/453 PH |
| 3,996,283 | 12/1976 | Knofel | 260/570 D |
| 4,061,678 | 12/1977 | Knöfel et al. | 260/570 D |
| 4,087,459 | 5/1978 | Knöfel et al. | 260/570 D |
| 4,093,658 | 6/1978 | Knöfel et al. | 260/570 D |
| 4,259,526 | 3/1981 | Dunlap et al. | 564/331 |
| 4,914,236 | 4/1990 | Knöfel et al. | 564/334 |
| 4,924,028 | 5/1990 | Knöfel et al. | 564/331 |

FOREIGN PATENT DOCUMENTS 2343658 3/1975 Fed. Rep. of Germany.

Primary Examiner—Richard L. Raymond
Attorney, Agent, or Firm—Joseph C. Gil

[57] ABSTRACT

The invention relates to an improved process for the production of polynuclear aromatic polyamines by condensation of aniline with formaldehyde in the presence of water and acidic catalysts and working up of the reaction mixture by extraction with a hydrophobic solvent, the acid catalyst accumulating in the aqueous phase of the extraction step being reused.

4 Claims, 3 Drawing Sheets

PROCESS FOR THE PRODUCTION OF POLYNUCLEAR AROMATIC POLYAMINES

BACKGROUND OF THE INVENTION

The present invention relates to an improved process for the production of polynuclear aromatic polyamines by condensation of aniline with formaldehyde in the presence of water and acidic catalysts and working up of the reaction mixture by extraction with a hydrophobic solvent, the acid catalyst accumulating in the aqueous phase of the extraction step being reused.

It is already known that the aqueous reaction mixture obtained in the production of polynuclear aromatic polyamines by condensation of aniline with formaldehyde in the presence of water and acidic catalysts can be worked up by extraction with a hydrophobic solvent and that the acid catalyst accumulating in the aqueous phase during the extraction step can be reused (see, e.g., German Offenlegungsschrift 2,343,658 and U.S. Pat. Nos. 3,996,283, 3,952,042, 4,061,678, 4,093,658, 4,087,459, and 4,259,526. The major advantage of the processes described in these publications is that the catalyst does not have to be neutralized because it accumulates in the aqueous phase during working up of the acidic reaction mixture by extraction and is returned as such to the beginning of the process and reused.

In addition, certain processes based on this known principle, as described for example, in U.S. Pat. Nos. 4,093,658 and 4,087,459, enable polyamine mixtures having either an increased or reduced content of 2,4'-isomers to be specifically produced as required.

In addition, the products of the processes according to the above-cited publications are suitable as intermediates for the production of polyisocyanates of the diphenyl methane series. However, it must be regarded as a disadvantage of the processes according to the above-cited publications that considerable quantities of hydrophobic solvent and aniline have to be used simply for working up the end products of the process by extraction, which of course involves considerable effort in terms of distillation and, hence, considerable energy consumption during working up of the organic phase by distillation.

A certain advance over the prior art cited above without losing any of its advantages was made by subsequently published processes, for example, those described in U.S. Pat. Nos. 4,914,236 and 4,924,028. The advantages of these processes apply in particular to product quality and product flexibility in addition to economic improvements. They are largely attributable to the use of a hydrophobic solvent, even while the reaction is in progress. Further advantages are afforded by the partial dual function of this hydrophobic solvent as a constituent both of the reaction mixture and of the extractant.

Overall, the state of the art as represented by U.S. Pat. Nos. 4,914,236 and 4,924,028 is distinguished by the following advantages:

1) The acid catalyst used is reused and is not destroyed by neutralization.
2) The mixtures accumulating as distillate during working up of the organic phase containing the end products by distillation may be reused as such, optionally after addition of more aniline, as extractant for the aqueous phase in the product extraction step without further separation into their constituents by distillation.
3) The processes are variable within wide limits in regard to the homolog distribution in the end products (ratio of diamines to higher polyamines).
4) The processes provide in particular for the production of polyamines of the diphenyl methane series having a relatively increased content of 2,4'-diaminodiphenyl methane and a small content of 2,2'-diaminodiphenyl methane which is always undesirable.

The disadvantage of these processes lies in the longer reaction times, particularly in the second rearrangement phase, to complete rearrangement into the desired end products which are attributable to the advantageous high selectivity of the reaction in two phases. This gives rise to the danger of incomplete rearrangement with the ensuing problems in regard to the quality of the end products and, above all, the polyisocyanates derived therefrom. Incomplete rearrangement means the presence of intermediate condensation products, for example of the N-aminobenzyl type, in the reaction mixture at the end of the actual reaction. During the working up of the reaction mixture to isolate the end products by any of the known processes, the intermediate and secondary products enter the end products of the process, resulting in considerable reductions in quality, particularly in the case of the resulting polyisocyanates. To avoid this by ensuring complete rearrangement at the end of the reaction, elaborate countermeasures in regard to the reaction time or reaction volume and/or the reaction temperature, particularly in the last rearrangement stage, have to be taken, particularly where they are carried out continuously.

In U.S. Pat. No. 4,914,236, the organic phase is removed at the end of the rearrangement reaction and is used to recover the end products of the process together with any intermediate condensation products present. These intermediate condensation products are present in higher concentrations in the organic phase than in the aqueous phase and enter the end product of the process with the organic phase through the working-up stage(s).

In U.S. Pat. No. 4,924,028, the condensation products present in the organic phase are converted by extraction into an aqueous phase after removal of the organic phase at the end of the rearrangement reaction and are recycled as such into the reaction. The remaining organic phase is then used elsewhere as extractant for the end products. During extraction with the aqueous phase, any intermediate condensation products present are initially concentrated in this organic phase by virtue of the selectivity of the process before finally passing over into the aqueous phase as the last components of the condensation product mixture. Accordingly, the extraction step has to be carried out quantitatively at considerable expense to ensure that the remaining, extracted organic phase can be safely reused as extractant for the end products of the process in the main extraction stage.

The problem addressed by the present invention was to provide a new improved process for the production of polynuclear aromatic polyamines from aniline and formaldehyde which would combine the advantages of the prior art and which would enable products of further improved quality to be produced without any of the disadvantages of the prior art, with less effort and

DESCRIPTION OF THE INVENTION

Figure 1:
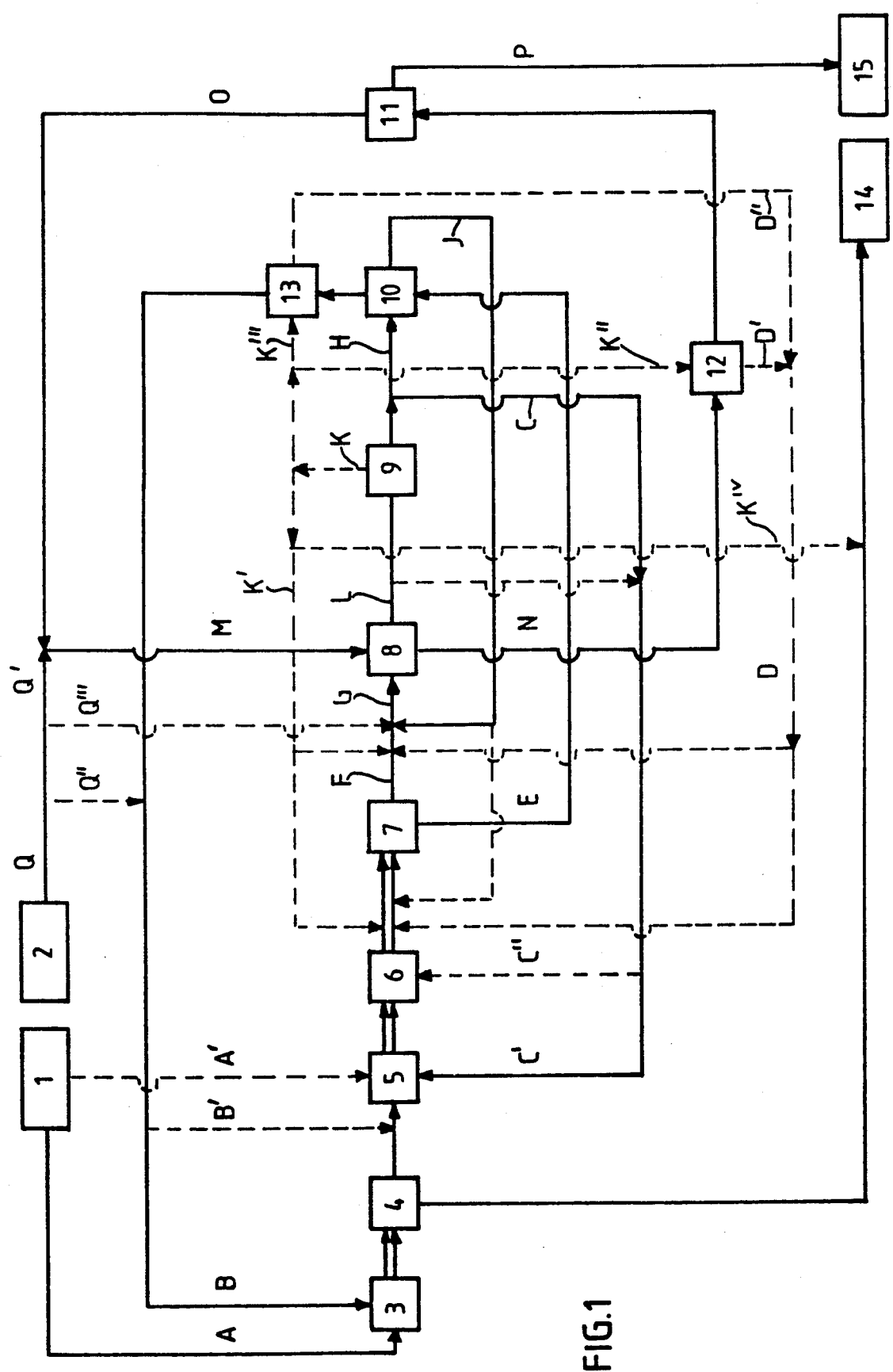
FIG. 1 represents a flow sheet for a first embodiment of the present invention.

The present invention relates to an improved process for the production of polynuclear aromatic polyamines by reaction of aniline with formaldehyde in the presence of water and acidic catalysts in a single or two stage reaction at a temperature of from 0° to 180° C., optionally preceded by a preliminary aminal stage in which N,N'-disubstituted aminal is formed and is then converted into the desired end product in one or more stages in the presence of acid catalyst at a temperature of from 0° to 180° C., working up of the resulting reaction mixture by extraction with an aniline-containing hydrophobic solvent in a product extraction stage, separation of the resulting organic phase by distillation into (i) a distillate consisting of aniline-containing solvent, which distillate is reused in the extraction stage, optionally after addition of fresh aniline, and (ii) a distillation residue consisting essentially of end product and recycling of aqueous phase accumulating during extraction and containing the acid catalyst, with reuse of the catalyst contained in the aqueous phase and removal of the water of condensation formed in the condensation reaction and of the water introduced into the process with the aqueous formaldehyde solution in a water separator placed downstream of the preliminary aminal stage and upstream of the first reaction stage and/or in an evaporator placed downstream of the extraction stage, the improvement wherein a) the formaldehyde is either reacted by mixing in a preliminary aminal stage with an organic phase consisting of aniline and hydrophobic solvent, and optionally aniline/formaldehyde condensates, and/or in a first reaction stage with an organic phase consisting of aniline and hydrophobic solvent, and optionally aniline/formaldehyde condensates, and with recycled aqueous phase containing the catalyst in the form of amine salts, b) the two-phase reaction mixture obtained is separated on completion of the reaction into an aqueous phase and an organic phase in a phase separator upstream of the product extraction stage, c) the organic phase accumulating in said phase separator is extracted in a post-extraction stage following the product extraction stage with at least a portion of the aqueous phase substantially freed from reaction product which accumulates in the product extraction stage, d) the aqueous phase accumulating in the post-extraction stage, which is enriched with reaction product of the organic phase accumulating in the phase separator is completely or at least partly recycled to the reaction after the completion of rearrangement and before the product extraction stage and any aqueous phase remaining is recycled before the completion of rearrangement, constisting of aniline and e) the organic phase hydrophobic solvent, and, optionally aniline/formaldehyde condensates, which accumulates in the post-extraction stage, is returned to the beginning of the process and reacted in accordance with a), f) the aqueous phase accumulating in the phase separator is extracted with aniline-containing hydrophobic solvent in the product extraction stage, optionally after combination with aqueous phase from the post-extraction stage, g) either 1) the aqueous phase accumulating in the product extraction stage is divided into two partial streams of which one is returned to the beginning of the process while the other is delivered to the post extraction stage, or 2) the aqueous phase accumulating in the product extraction stage is delivered to the post-extraction stage and is then divided into partial streams of which one is returned to the beginning of the process while the other is delivered to a point after the completion of the rearrangement reaction and before the product extraction stage, h) the organic phase accumulating in the product extraction stage is separated in the distillation stage into a distillate consisting of aniline-containing hydrophobic solvent and a distillation residue consisting essentially of end product, and i) the distillate accumulating in the distillation stage is used as extractant in the product extraction stage after addition of fresh aniline.

The following improvements are obtained by selective separation and internal recycling of intermediate condensation products to the reaction before recovery and isolation of the actual end products:

1. The isolated end products have an extremely low content of intermediate condensation products which, in every case, is distinctly lower than in the reaction products at the end of the actual reaction, so that 2. a higher content of intermediate condensation products can be tolerated in the end reaction products than in the state-of-the-art processes without any adverse effect on the end products of the process or their derivatives.

3. In addition, the process according to the invention offers additional safety in regard to the quality of the end products against "breakthrough" of intermediate condensation products into the isolated end products if increased levels of these intermediate products occur through variations and disturbances in the process at the end of the rearrangement reaction.

4. After working up, the isolated end products always have a lower content of 2,2'-diaminodiphenyl methane than the end reaction products.

5. The isolated end products may also have a lower content of 2,4'-diaminodiphenyl methane than the end reaction products.

6. The content of 2,4'-diaminodiphenyl methane in the end products can be controlled within wide limits irrespective of the actual reaction parameters, such as the (condensation) ratio of aniline to formaldehyde, the ratio of amine to catalyst (i.e., degree of protonation) and the phase ratio of organic to aqueous phase during the reaction.

7. The isolated end products may also have a lower content of ortho-substituted higher homologs of the diaminodiphenyl methane than the end reaction products Starting materials for the process according to the invention are aniline and formaldehyde or formaldehyde donors. The formaldehyde is preferably used in the form of an aqueous solution having a formaldehyde content of from 20 to 50% by weight.

The hydrophobic solvents used are inert solvents boiling at temperatures in the range from 30° to 250° C. and preferably from 80° to 200° C., such as for example, chlorobenzene. dichlorobenzenes, benzene, toluene, xylene, dichloroethane, chloroform or carbon tetrachloride. Xylenes, i.e. technical xylene mixtures, are preferably used as the hydrophobic solvent, with o-xylene being particularly preferred.

The acid catalyst is selected from water-soluble acids having a pKa value below 2.5 and preferably below 1.5. Examples include hydrochloric acid, hydrobromic acid, sulfuric acid, trifluoroacetic acid, methane sulfonic acid or phosphoric acid. Hydrochloric acid is preferably used as the catalyst. The acids mentioned may also be used in admixture with acidic or neutral salts of such acids, such as for example, the corresponding ammonium salts or even the corresponding alkali metal salts. However, the use of such salts is less preferred. The acids mentioned are present in the recycle system according to the invention in the form of the corresponding ammonium salts of the bases present in the water-based circuit.

The process according to the invention may be carried out both in a single stage and in two stages with or without inclusion of a preliminary aminal stage, with the proviso that, where the reaction is carried out in a single stage, a preliminary aminal stage should always be included.

By "single-stage reaction" is meant an embodiment of the process in which the aminal is heated to an elevated temperature of 60° to 180° C. and preferably 80° to 150° C. over a short period of less than 10 minutes and preferably less than 5 minutes after addition of the acid catalyst and is rearranged into the end product at that temperature or in which the aminal is directly mixed with the recirculated aqueous catalyst phase heated to the elevated temperature of 60° to 180° C. and preferably 80° to 150° C. and the resulting mixture is then optionally heated to the desired final temperature.

By "two-stage reaction" is meant an embodiment in which, after addition of the acid catalyst, the reaction mixture of aniline, formaldehyde and acid catalyst, is first kept at 0° to 60° C. and preferably 30° to 60° C. for 10 to 90 minutes and preferably 15 to 60 minutes in a first reaction stage and then at 60° to 180° C., preferably at 60° to 150° C. and more preferably at 95° to 145° C. for 30 to 180 minutes and preferably for 30 to 120 minutes in a second reaction stage. In this preferred embodiment of a multi-stage and preferably two-stage reaction, the first stage comprises the rearrangement of the aminal or (in the absence of a preliminary aminal stage) the condensation of the starting materials to N-benzyl aniline which, in the second stage of the reaction, is rearranged at elevated temperature to the nucleus-substituted end product. In one preferred embodiment in which the reaction is carried out in two stages with or preferably without a preliminary aminal stage, the first stage is initiated with only a partial stream of the aqueous catalyst phase, generally less than 50% and preferably less than 15%. In the further course of the first reaction stage and before the last, i.e. generally the second, reaction stage is completed, the reaction is completed in the presence of the entire catalyst phase.

The process may be carried out both continuously and discontinuously. In the continuous embodiment, the times indicated relate to the average residence time of the reaction mixture in the individual stages. Where a preliminary aminal stage is included, the (average) residence time of the starting materials in this stage is generally 10 to 60 minutes and preferably from 15 to 60 minutes. The temperature in the preliminary aminal stage is generally in the range from 20° to 100° C. and preferably in the range from 20° to 60° C. In all stages, the process is preferably carried out under the natural pressure of the system and preferably in an inert gas atmosphere (such as nitrogen).

Figure 2:
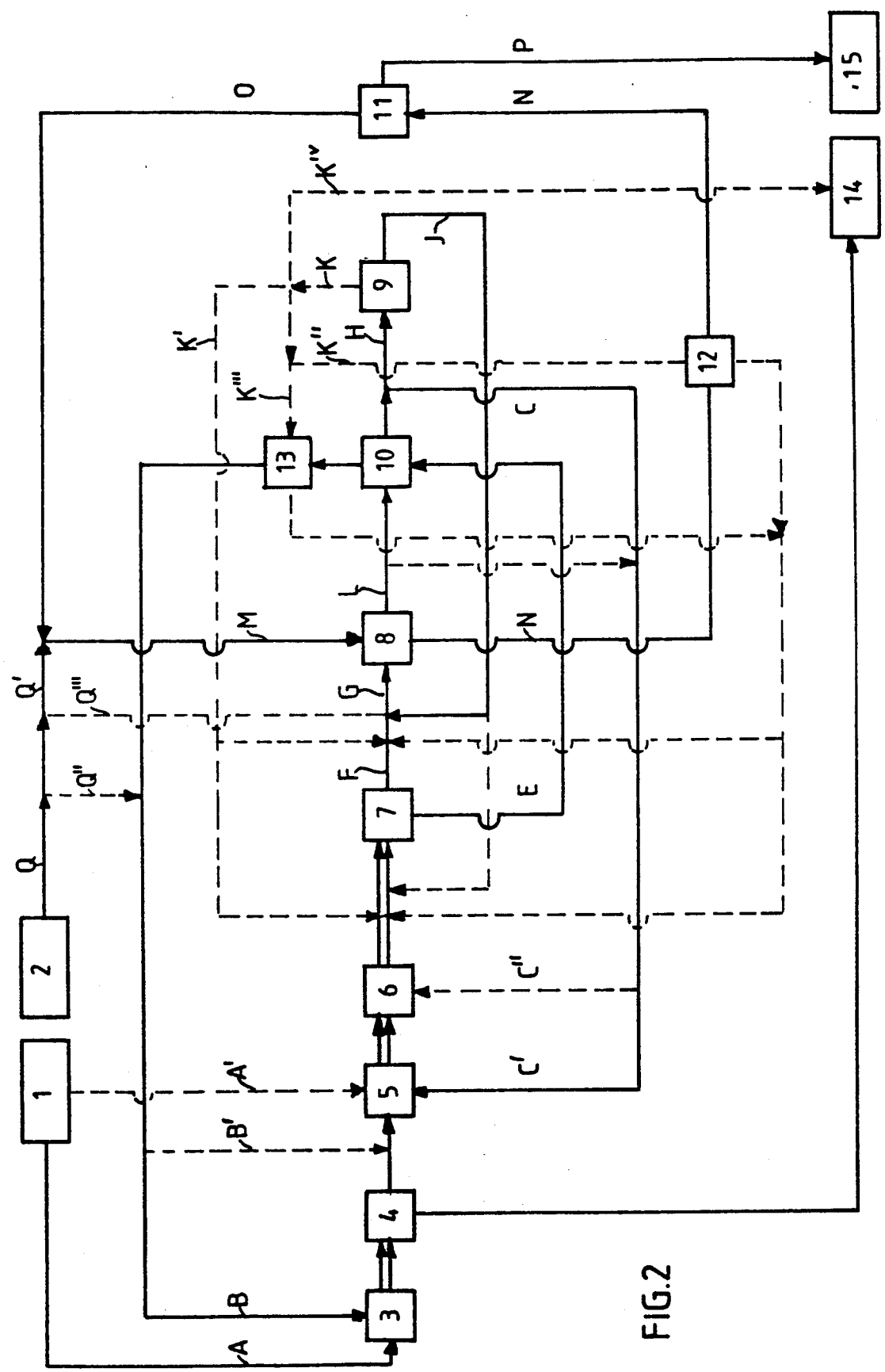
FIG. 2 represents a flow sheet for a second embodiment of the present invention.

The process according to the invention is illustrated by the flow charts shown in FIGS. 1 and 2 where the reference numerals have the following meanings:

(1) a tank for aqueous formaldehyde solution
(2) a tank for aniline
(3) a condensation reactor (preliminary aminal stage)
(4) a water separator
(5) the first reaction stage
(6) the second reaction stage
(7) a phase separator
(8) the product extraction stage
(9) a water evaporator
(10) the post-extraction stage
(11) the product distillation stage
(12) a washing stage
(13) a washing stage
(14) a tank for wastewater and
(15) a tank for end product.

The references A to Q denote the flow streams which are referred to both in the following and in the Examples.

In the above-mentioned embodiment where the reaction is carried out in a single stage, the reaction stages (5) and (6) are combined into a single reaction stage. Both the first and the second reaction stage may consist both of a single reactor and of several reactors arranged in series. Cascades of stirred tanks and/or column reactors arranged in series have proved to be particularly suitable for maintaining the residence times mentioned.

The extraction stage may also consist of one or more extractors arranged in series. Typical countercurrent extractors are preferably used for the extraction stage.

In the most simple case, the distillation stage (11) consists of a distillation column which is designed in such a way that the hydrophobic solvent and aniline can largely be separated from the end product.

One particular advantage of the process according to the invention lies in the fact that there is no need for the hydrophobic solvent and the aniline to be separated because the aniline content in the distillate generally does not exceed the value required for reuse which, before reuse, is adjusted as required by addition of fresh aniline, so that energy-saving multistage distillation techniques can be used to solve the distillation problem.

Accordingly, the distillation stage (11) is preferably operated in several stages by a procedure in which a distillate fraction containing the relatively low-boiling hydrophobic solvent in relatively enriched form in addition to aniline in relatively depleted form is obtained in a first distillation stage and a distillate fraction containing the hydrophobic solvent in relatively depleted form and the aniline in relatively enriched form is obtained in a final distillation stage, the distillation process as a whole being carried out with maximal utilization of the distillation energy applied. In one preferred embodiment, aniline substantially free from hydrophobic solvent is obtained as distillate in a final distillation stage.

The water formed during the condensation reaction and the water introduced into the system with the aqueous formaldehyde solution has to be removed from the system at a suitable point to maintain a constant water volume. Where a preliminary aminal stage (3) is included, this removal of water preferably takes place in the water separator (4) before the aminal is combined with the acid catalyst. In the absence of a preliminary aminal stage, the water is preferably removed in a water evaporator (9) arranged after the product extraction stage (8). The water evaporator is preferably operated on the principle of flash evaporation by application of vacuum.

Basically, however, it is also possible to remove water from the system by distillation at any other point.

There are several embodiments for carrying out the process according to the invention, as described in detail hereinafter.

In a first embodiment, the aqueous formaldehyde solution (A) is fed into the aminal stage (3) in which the reaction with the mixture (B) of aniline, optionally aniline/formaldehyde condensates and hydrophobic solvent takes place. The flow stream (B) consists essentially of the organic phase leaving the post-extraction stage (10) or the washing stage (13) to which aniline is optionally added from the storage tank (2).

The molar ratio of aniline to formaldehyde in the aminal stage is generally between 1.5:1 and 25:1 and preferably between 1.8:1 and 10:1.

The ratio by weight of aryl amine (i.e., aniline and any aniline/formaldehyde condensates present) to hydrophobic solvent in (B) is generally between 1:4 and 3:1 and preferably between 1:2 and 2:1.

The reaction in the aminal stage (3) takes place at a temperature within the ranges mentioned above.

The mechanical separation of the aqueous phase, which is formed by the water of condensation and the water of the aqueous formaldehyde solution, and which, in addition, contains the water-soluble impurities of the formaldehyde and the flow stream (B), takes place in a separator (4) after the aminal stage (3), preferably at a temperature below 60° C.

The remaining organic phase is transferred to the reactor (5) and combined with the aqueous flow stream (C') at temperatures below 60° C.

In this first embodiment, the flow stream (C') consists of the total quantity of catalyst phase (C) to be recycled. The content of aniline/formaldehyde condensates in this phase (C) is generally below 5% by weight and preferably below 2% by weight for a total content of aryl amine (including aniline) at this point of generally 30 to 70% by weight and preferably 40 to 60% by weight for a degree of protonation of 25 to 75 and preferably 45 to 70%. Both here and in the following, the "degree of protonation" is understood to be the percentage of amine nitrogen atoms which are present in the form of ammonium groups, i.e. "protonated".

The ratio by weight of organic phase from (4) to catalyst phase (C) is generally between 100:1 and 1:10 and preferably between 4:1 and 1:3.

In the first continuous embodiment of the process according to the invention, the reactor (5) represents the "first reaction stage" mentioned above which is operated under the above-mentioned conditions in regard to temperature and reaction time. The reactor is generally a multistage cascade of stirred tanks or a single-stage or multistage column reactor in which the temperature preferably passes through a profile increasing from about 20° C. at the beginning to 60° C. at the end.

The two-phase reaction mixture is transferred from the first reaction stage (5) to the second reaction stage (6) which also consists of a multistage cascade of stirred tanks or a single-stage or multistage column reactor. This second reaction stage is also operated under the above-mentioned conditions in regard to reaction temperature and average residence time. In the reaction stage (6), the two-phase reaction mixture preferably passes through a temperature profile beginning at 60° C. and ending at a temperature of 90° to 150° C. and preferably at a temperature of 95° to 140° C. With this preferred temperature profile, residence times of up to 60 minutes are generally sufficient in the reaction stage (6).

The two-phase reaction mixture leaving the second reaction stage (6) is then divided in the phase separator (7), preferably at temperatures of 80° to 110° C., into an organic phase (E) and an aqueous phase (F) which is optionally combined with the stream (J) to form the aqueous phase (G) and delivered to the product extraction stage (8).

The end products are extracted in exchange for aniline from the aqueous phase (G) in the preferably multistage extractor (8) which is preferably operated at temperatures of 80° to 110° C., and are converted into an organic solution (N).

A mixture of hydrophobic solvent and aniline is used as the extractant (M). The ratio by weight of aniline to solvent is generally between 0.5:1 and 3:1 and preferably between 1:1 and 2:1.

The ratio by weight of extractant (M) to aqueous phase (6) is generally between 0.5:1 and 3:1 and preferably between 0.7:1 and 2:1.

The organic phase (N) is transferred to the distillation stage (11), optionally after passing through a catalyst washing stage (12) where any traces of catalyst are removed.

A distillation residue (P), which represents the end product and is collected in the tank (15), is separated by distillation in the distillation stage (11). The distillation stage (11) may consist, for example, of a single-stage evaporator which, in addition to the distillation residue (P) gives a distillate (0).

In addition to aniline, the distillate (0) contains the entire hydrophobic solvent from (N) and is used as the extractant (M), optionally after addition of fresh aniline (Q').

The aqueous phase (L) leaving the product extraction stage (8) contains only very small amounts of less than 5% by weight and preferably less than 2% by weight of process products (aniline/formaldehyde condensates) and is divided into two partial streams C and H, the ratio by weight of C to H generally being from 1:100 to 10:1 and preferably from 1:3 to 3:1. The partial stream C is returned as aqueous catalyst solution to the first reaction stage (5) (C=C'). With the partial stream H, the organic phase (E) is extracted from the separator (7) in the multistage post-extraction stage (10), which is generally operated at temperatures of 40° to 110° C., process products present in (E) being largely exchanged for aniline and transferred to the aqueous phase (J) so that an organic phase (B) poor in condensation products is obtained.

The residual content of process products in (B) is generally less than 10% by weight and preferably less than 5% by weight. This residue of condensation products contains inter alia the 2,2'-isomer of diaminodiphenyl methane in relatively enriched form.

The intermediate condensation products which may still be present in the reaction mixture at the end of the rearrangement reaction in (6) also initially remain substantially quantitatively in the organic phase (E) during phase separation in the separator (7) in the present embodiment. On passing through the post-extraction stage (10), the intermediate condensation products are concentrated in the residual fraction and are subsequently recycled with the flow stream (B).

The organic phase (B) accumulating in the post-extraction stage (10) is returned to the aminal stage (3), optionally after addition of aniline (Q") for example from the storage tank (2).

The aqueous phase (J) accumulating in the post-extraction stage (10) is returned to the reaction between the last reaction stage (6) and the main extraction stage (8) and preferably between (7) and (8) where it is combined with the aqueous phase (F) from the phase separator (7) to form the aqueous phase (G).

In the first embodiment of the process according to the invention, the water evaporator mentioned above is preferably arranged between the product extraction stage (8) and the post-extraction stage (10), the division of the flow stream (L) into the streams (C) and (H) taking place before or after the evaporator. In the water evaporator (9) water is removed from the aqueous solution (L or H) in a quantity (K) which generally makes up as much as 80% by weight, but preferably less than 50% by weight, of the quantity of water in the aqueous phase introduced into the evaporator. The quantity (K) of water is preferably returned to the reaction mixture (K') between the second reaction stage (61 and the product extraction stage (8), but may optionally be used at least partly beforehand to wash the organic phase leaving the product extraction stage (8) to remove traces of acid (K") and/or to wash the organic phase (B) (K")' to be returned to the beginning of the process, with the aqueous phases (D') and (D") resulting in the particular washing stages (12) and (13).

Where this procedure is adopted (removal of water in (9) and recycling), the rearrangement reaction in the reactors (5) and (6) is carried out with a lower water content in the aqueous phase than extraction in the extraction stage (8).

In another embodiment of the process according to the invention, the aminal stage (3) is partly or completely omitted. In practice, this means that a partial amount of the mixture of aryl amine and hydrophobic solvent (B') used in the reaction and/or a partial quantity of the aqueous formaldehyde (A') used is/are not introduced into the aminal stage (3), but instead before or into the first reaction stage (5) In the extreme case (complete omission of the preliminary aminal stage), the total quantity of the mixture of aniline and hydrophobic solvent and the total quantity of aqueous formaldehyde may even be directly introduced into the first reaction stage (5). In the absence of the preliminary aminal stage, however, the reaction must always be carried out in two stages, as mentioned above, using the reaction stages (5) and (6). Where such a procedure is adopted, the water introduced and the water formed by condensation is of course removed only partly, if at all, through the phase separator (4). This water is then removed, for example, from the distillate from (10) as flow stream $K^{IV}$ which is directly introduced into the wastewater tank (14).

In yet another embodiment, the reaction stages (5) and (6) may be combined into a single reaction stage which is operated under the above-described conditions in regard to reaction temperature and reaction time. However, where the reaction is carried out in a single stage, a preliminary aminal stage (3) must always be included.

The reaction in the first stage may also take place in the presence of only a part (C') of the recycled catalyst solution and with addition of the remaining quantity of catalyst solution (C", C''' and $C^{IV}$) after the first reaction stage (5) and before the product extraction stage (8). This embodiment is preferably carried out by separating the catalyst stream (C) into two partial streams (C') and (C") and introducing the first partial stream (C') into the first reaction stage (5) and the second partial stream (C") into the reaction mixture in the further course of the first reaction stage (5) and before or during the second reaction stage (6). The ratio by weight between organic phase in (5) and aqueous phase (C') initially introduced, for example in the first stirred tank of (5), is between 1:1 and 100:1 and preferably between 3:1 and 30:1.

One feature common to the described variants of the process according to the invention is that, in the post-extraction stage (10), the reaction products present in (E) i.e. the fraction of the reaction products present at the end of the actual reaction part (6) and separated in the separator (7) with (E), are preferably separated substantially selectively into:

1. a residual fraction remaining in the organic phase leaving the post-extraction stage (10). The constituents already enriched in (E) in relation to (F), such as intermediate condensation products of the N-aminobenzyl amine type, optionally of the aminal type, end condensation products, such as 2,2'-diaminodiphenyl methane, optionally 2,4'-diaminodiphenyl methane and optionally other unspecified intermediate products, end products and/or secondary products, are concentrated in this residual fraction and are recycled with the organic phase (B) to the beginning of the reaction,
2. a product fraction which is present in the aqueous phase (J) and in which the product components mentioned in I. are relatively depleted. According to the invention, the product fractions present in the aqueous phase (J) pass into the extraction stage (8) and hence into the isolated end product of the process either indirectly via process stage (7) or preferably directly by combination of (J) with the aqueous phase (F) to form the stream (G).

In this way, the ratio of 2,2'-isomers to 2,4'-isomers in the isolated end products of the process can generally be kept below 1:20, even despite relatively high contents of the 2,4'-isomer, for example of more than 10% of the total content of diaminodiphenyl methane. The percentage content of 2,2'-diaminodiphenyl methane in the end product isolated is generally less than 50% of the content of comparable products which have not been produced by the process according to the invention.

Basically, the organic phase (8) delivered to the distillation stage (11) should be substantially free from acid traces. This can be achieved by intensive washing in the washing stage (12) and/or by neutralization in a neutralization stage (not shown).

Figure 3:
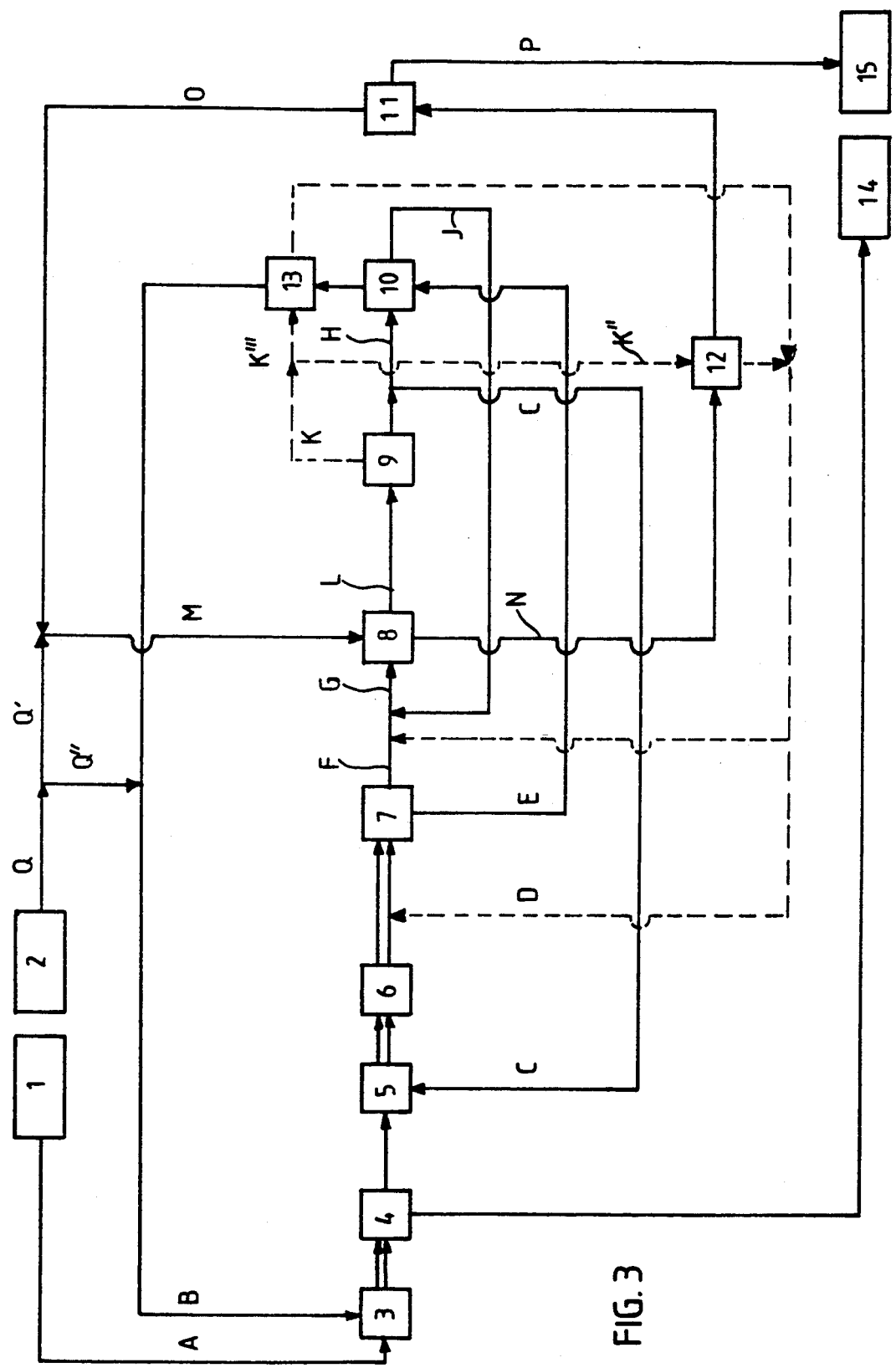
FIG. 3 represents a flow diagram for the process used in Example 1.

The process according to the invention is illustrated by the following Examples:

Example 1 (see FIG. 3)

In a reactor (3) consisting of two stirred tanks arranged in tandem, 30% aqueous formalin solution (stream A) is reacted at 40° C. with an aniline/xylene mixture still containing polyarylamine components (stream B):

A) 0.62 kg/h formaldehyde
1.45 kg/h water
B) 0.06 kg/h polyarylamine
4.07 kg/h aniline
3.55 kg/h orthoxylene.

In the following separator (4), the lower aqueous phase is removed as wastewater and collected in the waste-water tank (14).

The upper organic phase is transferred to a second reactor (5) consisting of three stirred tanks and is mixed therein with stream (C) containing the acidic catalyst:

C) 0.04 kg/h polyarylamine
1.69 kg/h aniline
0.40 kg/h hydrogen chloride
2.38 kg/h water The measured and regulated temperatures in the three tanks of the reactor (5) are 30° C., 40° C. and 60° C.

In another reactor (6), which also consists of three stirred tanks, the temperatures are 100° C., 135° C. and 140° C. and are established by heating under the natural pressure of the system.

After cooling of the reaction mixture to 95° C. and expansion to normal pressure and after addition of the HCl washing water from the extraction stages (12) and (13) the organic phase (stream E) and the aqueous phase (stream F) are separated from one another in the phase separator (7):

E) 1.81 kg/h polyarylamine
1.61 kg/h aniline
3.55 kg/h orthoxylene
F) 1.89 kg/h polyarylamine
0.81 kg/h aniline
0.40 kg/h hydrochloric acid
3.88 kg/h water.

The aqueous phase (F), together with the aqueous phase (I) from the post-extraction stage (10), is then continuously extracted with a mixture of aniline and xylene (stream M) in the countercurrent extraction column (8):

M) 8.45 kg/h aniline
7.05 kg/h orthoxylene and is converted into the polyarylamine-depleted aqueous phase (stream L):

L) 0.08 kg/h polyarylamine
3.28 kg/h aniline
0.77 kg/h hydrochloric acid
7.41 kg/h water.

The partial stream (L) is concentrated in the distillation stage (9) with removal of distillate as stream (K) and is subsequently divided into two partial streams (C) and (H).

C) 4.50 kg/h
H) 4.24 kg/h

The stream (H) is used in another extraction column (10) for countercurrent extraction of the organic phase (E) separated in (7).

The aqueous phase (stream (J)) resulting in (10), which is enriched with polyarylamine in relation to the aqueous partial stream (H) used is combined with the aqueous phase (F) from the separator (7) and concentrated therewith as stream (6) in (8).

J) 1.78 kg/h polyarylamine
1.31 kg/h aniline
0.31 kg/h hydrochloric acid
2.24 kg/h water.

After passage through the washing stage (13) and addition of aniline (Q"), the organic phase obtained in the extraction stage (10) which is depleted with polyaryl-amine in relation to (E), is returned to the reactor (3) as stream (B).

The organic phase containing the reaction product accumulating in the product extraction stage (8) (stream N) is extracted with most of the distillate of the distillation stage (9) consisting essentially of water in another three- to five-stage extraction column (12) (stream $K^{II}$).

N) 3.59 kg/h polyarylamine
7.30 kg/h aniline
7.05 kg/h orthoxylene
$K^{II}$) approx. 2.8 kg/h water.

In the washing stage (12), the HCl content of stream (N), which is approximately 0.2% by weight, is reduced to <0.01% by weight. The HCl-containing washing water (approx. 2.8 kg/h) is recycled into the reaction mixture as stream (D).

After removal of remaining traces of acid by neutralization with excess sodium hydroxide and removal of the sodium chloride formed and the unused sodium hydroxide, the organic phase leaving the washing column (12) is separated in a distillation stage (11) into a distillate (stream O) and a distillation residue (stream P):

O) 7.30 kg/h aniline
7.05 kg/h orthoxylene
P) approx. 3.5 kg/h polyarylamine

By addition of fresh aniline (Q') from the storage tank (2) to the distillate (O), the extractant required in (8) is adjusted both in quantity and in composition (stream M).

The distillation residue (stream P) of the distillation stage (9) has the following composition:

0.4% by weight 2,2'-diaminodiphenyl methane
9.7% by weight 2,4'-diaminodiphenyl methane
59.7% by weight 4,4'-diaminodiphenyl methane
0.2% by weight N-substituted diaminodiphenyl methanes
19.2% by weight triamines
6.0% by weight tetramines
approx. 4.8% by weight higher than tetrafunctional polyamines.

Example 2

In a reactor (3) consisting of two stirred tanks arranged in tandem, 30% aqueous formalin solution (stream A) is reacted at 40° C. with an aniline/xylene mixture still containing polyarylamine components (stream B):

A) 0.62 kg/h formaldehyde
1.45 kg/h water
B) 0.22 kg/h polyarylamine
3.82 kg/h aniline
3.26 kg/h orthoxylene.

In the following separator (4), the lower aqueous phase is removed as wastewater and collected in the waste-water tank (14). The upper organic phase is transferred to a second reactor (5) consisting of three stirred tanks and is mixed therein with stream (C) containing the acidic catalyst:

C) 0.07 kg/h polyarylamine
2.21 kg/h aniline
0.54 kg/h hydrogen chloride
3.18 kg/h water The measured and regulated temperatures in the three tanks of the reactor (5) are 30° C., 40° C. and 60° C.

In another reactor (6), which also consists of three stirred tanks, the temperatures are 100° C., 135° C. and 140° C. and are established by heating under the natural pressure of the system.

After cooling of the reaction mixture to 95° C. and expansion to normal pressure and after addition of the HCl washing water from the extraction stages (12) and (13) the organic phase (stream E) and the aqueous phase (stream F) are separated from one another in the phase separator (7):

E) 1.48 kg/h polyarylamine
1.37 kg/h aniline
3.26 kg/h orthoxylene
F) 2.40 kg/h polyarylamine
1.32 kg/h aniline
0.54 kg/h hydrochloric acid
4.98 kg/h water.

The aqueous phase (F) together with the aqueous phase (J) from the post-extraction stage (10) is then continuously extracted with a mixture of aniline and xylene (stream M) in the countercurrent extraction column (8):

M) 8.9 kg/h aniline
8.1 kg/h orthoxylene and is converted into the polyarylamine-depleted aqueous phase (stream L):
L) 0.12 kg/h polyarylamine
3.68 kg/h aniline
8.30 kg/h water.

The stream (L) is divided into two partial streams (C) and (H).

C) 5.20 kg/h
H) 7.80 kg/h

The partial stream (C) is concentrated in the distillation stage (9) with removal of distillate as stream (K) and is subsequently returned as stream (C) to the reactor (5). The partial stream (H) is used in another extraction column (10) for countercurrent extraction of the organic phase (6) separated in (7).

The aqueous phase (stream (J)) resulting in (10), which is enriched with polyarylamine in relation to the aqueous partial stream (H) used is combined with the aqueous phase (F) from the separator (7) and extracted therewith in (8).

(J) 1.30 kg/h polyarylamine
1.12 kg/h aniline
0.36 kg/h hydrochloric acid
3.32 kg/h water.

After passage through the washing stage (13), the organic phase obtained in the extraction stage (10) which is depleted with polyarylamine in relation to (E), is returned to the reactor (3) as stream (B).

The organic phase containing the reaction product accumulating in the product extraction stage (8) (stream N) is extracted with the distillate of the distillation stage (9) consisting essentially of water in another extraction column (12) (stream K).

N) 3.59 kg/h polyarylamine
7.66 kg/h aniline
8.10 kg/h orthoxylene K) 1.50 kg/h water.

In the washing stage (12), the HCl content of stream (N) which is approximately 0.2% by weight, is reduced to 0.01% by weight.

The HCl-containing washing waters (approx. 1.8 kg) from (12) and (13) are recycled into the reaction mixture as stream (D).

After removal of remaining traces of acid by neutralization with excess sodium hydroxide and removal of the sodium chloride formed and the unused sodium hydroxide, the organic phase leaving the washing column (12) is separated in a distillation stage (11) into a distillate (stream O) and a distillation residue (stream P):

O) 7.66 kg/h aniline
8.10 kg/h orthoxylene
P) approx. 3.5 kg/h polyarylamine.

By addition of fresh aniline (Q) from the storage tank (2) to the distillate (O), the extractant required in (8) is adjusted both in quantity and in composition (stream M).

The distillation residue (stream P) of the distillation stage (11) has the following composition:

<0.2% by weight 2,2'-diaminodiphenyl methane
6.7% 2,4'-diaminodiphenyl methane
60.3% by weight 4,4'-diaminodiphenyl methane
<0.2% by weight N-substituted diaminodiphenyl methanes
20.2% by weight triamines
7.5% by weight tetramines
approx 4.9% by weight higher than tetrafunctional polyamines.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for the production of polynuclear aromatic polyamines by reaction of aniline with formaldehyde in the presence of water and acidic catalysts in a single or two stage reaction at a temperature of from 0° to 180° C., optionally preceded by a preliminary aminal stage in which N,N'-disubstituted aminal is formed and is then converted into the desired end product in one or more stages in the presence of acid catalyst at a temperature of from 0° to 180° C., working up of the resulting reaction mixture by extraction with an aniline-containing hydrophobic solvent in a product extraction stage, separation of the resulting organic phase by distillation into (i) a distillate consisting of aniline-containing solvent, which distillate is reused in the extraction stage, optionally after addition of fresh aniline, and (ii) a distillation residue consisting essentially of end product and recycling of aqueous phase accumulating during extraction and containing the acid catalyst, with reuse of the catalyst contained in the aqueous phase and removal of the water of condensation formed in the condensation reaction and of the water introduced into the process with the aqueous formaldehyde solution in a water separator placed downstream of the preliminary aminal stage and upstream of the first reaction stage and/or in an evaporator placed downstream of the extraction stage, the improvement wherein a) the formaldehyde is either reacted by mixing in a preliminary aminal stage with an organic phase consisting of aniline and hydrophobic solvent, and optionally aniline/formaldehyde condensates, and- /or in a first reaction stage with an organic phase consisting of aniline and hydrophobic solvent, and optionally aniline/formaldehyde condensates, and with recycled aqueous phase containing the catalyst in the form of amine salts, b) the two-phase reaction mixture obtained is separated on completion of the reaction into an aqueous phase and an organic phase in a phase separator upstream of the product extraction stage, c) the organic phase accumulating in said phase separator is extracted in a post-extraction stage following the product extraction stage with at least a portion of the aqueous phase substantially freed from reaction product which accumulates in the product extraction stage, d) the aqueous phase accumulating in the post-extraction stage, which is enriched with reaction product of the organic phase accumulating in the phase separator is completely or at least partly recycled to the reaction after the completion of rearrangement and before the product extraction stage and any aqueous phase remaining is recycled before the completion of rearrangement, e) the organic phase consisting of aniline and hydrophobic solvent, and, optionally aniline/formaldehyde condensates, which accumulates in the post-extraction stage, is returned to the beginning of the process and reacted in accordance with a), f) the aqueous phase accumulating in the phase separator is extracted with aniline-containing hydrophobic solvent in the product extraction stage, optionally after combination with aqueous phase from the post-extraction stage, g) either 1) the aqueous phase accumulating in the product extraction stage is divided into two partial streams of which one is returned to the beginning of the process while the other is delivered to the post extraction stage, or 2) the aqueous phase accumulating in the product extraction stage is delivered to the post-extraction stage and is then divided into partial streams of which one is returned to the beginning of the process while the other is delivered to a point after the completion of the rearrangement reaction and before the product extraction stage, h) the organic phase accumulating in the product extraction stage is separated in the distillation stage into a distillate consisting of aniline-containing hydrophobic solvent and a distillation residue consisting essentially of end product, and i) distillate accumulating in the distillation stage is used as extractant in the product extraction stage after addition of fresh aniline.

2. The process of claim 1, wherein before or after step g), water is removed by distillation in a second distillation stage from the aqueous phase leaving the product extraction stage in a quantity exceeding the quantity of water required to maintain a constant volume in the circuit and this quantity of water exceeding the quantity required to maintain a constant water volume is returned to the circuit at any point after the rearrangement and before the product extraction stage.

3. The process of claim 2, wherein, before it is recycled, the water accumulating as distillate in the second distillation stage is at least partly used to wash the organic phase leaving the product extraction stage and/or the organic phase leaving the post-extraction stage.

4. The process of claim 1, wherein catalyst solution to be returned to the beginning of the process is divided into two or more partial streams of which the first partial stream is returned to the first reaction stage while the other partial streams are returned to the reaction mixture after the first reaction stage and before the product extraction stage.

* * * * *